United States Patent
Komistek (10) Patent No.: US 10,932,915 B2
(45) Date of Patent: Mar. 2, 2021

(54) MOMENT INDUCED TOTAL ARTHROPLASTY PROSTHETIC

(71) Applicant: DEPUY IRELAND UNLIMITED COMPANY, Cork (IE)

(72) Inventor: Richard D Komistek, Knoxville, TN (US)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 88 days.

(21) Appl. No.: 16/036,148

(22) Filed: Jul. 16, 2018

(65) Prior Publication Data

US 2018/0318094 A1 Nov. 8, 2018

Related U.S. Application Data

(60) Continuation of application No. 14/963,293, filed on Dec. 9, 2015, now Pat. No. 10,045,849, which is a
(Continued)

(51) Int. Cl.
  *A61F 2/38* (2006.01)
  *A61F 2/30* (2006.01)
  *A61F 2/28* (2006.01)

(52) U.S. Cl.
  CPC .............. *A61F 2/38* (2013.01); *A61F 2/3836* (2013.01); *A61F 2/3868* (2013.01); *A61F 2/3886* (2013.01); *A61F 2/389* (2013.01); *A61F 2/3859* (2013.01); *A61F 2002/2892* (2013.01); *A61F 2002/30016* (2013.01); *A61F 2002/30199* (2013.01); *A61F 2002/30316* (2013.01); *A61F 2002/30324* (2013.01);
(Continued)

(58) Field of Classification Search
  CPC ....... A61F 2/3868; A61F 2/389; A61F 2/2892
  See application file for complete search history.

(56) References Cited

U.S. PATENT DOCUMENTS 3,765,033 A 10/1973 Goldberg
3,840,905 A 10/1974 Deane
(Continued)

FOREIGN PATENT DOCUMENTS

DE 19529824 A1 2/1997
EP 732091 B1 12/2001
(Continued)

OTHER PUBLICATIONS

Andriacchi, T.P., "The Effect of Knee Kinematics, Gait and Wear on the Short and Long-Term Outcomes of Primary Knee Replacement," NIH Consensus Development Conference on Total Knee Replacement, p. 61-62, (Dec. 8-10, 2003), (4 Pgs).
(Continued)

*Primary Examiner* — Rebecca S Preston (57) ABSTRACT

A prosthetic total knee replacement system comprises a distal femoral implant component, a tibial tray implant component and a fixed bearing tibial tray insert. The fixed bearing tibial tray insert is fixed to the tibial tray and articulates with the distal femoral implant component. The fixed bearing tibial tray insert component has a medial-lateral centerline and a stabilizing post. The stabilizing post has a medial-lateral centerline offset laterally from the medial-lateral centerline of the fixed bearing tibial tray insert.

6 Claims, 9 Drawing Sheets

Related U.S. Application Data division of application No. 14/132,343, filed on Dec. 18, 2013, now Pat. No. 9,254,197, which is a division of application No. 12/203,987, filed on Sep. 4, 2008, now Pat. No. 8,636,807, which is a continuation of application No. PCT/US2006/010431, filed on Mar. 21, 2006.

(52) U.S. Cl.
CPC ............. *A61F 2002/30326* (2013.01); *A61F 2002/30329* (2013.01); *A61F 2002/30331* (2013.01); *A61F 2002/30354* (2013.01); *A61F 2002/30362* (2013.01); *A61F 2002/30364* (2013.01); *A61F 2002/30385* (2013.01); *A61F 2002/30518* (2013.01); *A61F 2002/30604* (2013.01); *A61F 2002/30624* (2013.01)

(56) References Cited

U.S. PATENT DOCUMENTS

| | | |
|---|---|---|
| 3,869,731 A | 3/1975 | Waugh |
| 4,209,861 A | 7/1980 | Walker |
| 4,215,439 A | 8/1980 | Gold |
| 4,249,270 A | 2/1981 | Bahler |
| 4,262,368 A | 4/1981 | Lacey |
| 4,340,978 A | 7/1982 | Buechel |
| 4,470,158 A | 9/1984 | Pappas |
| 4,888,021 A | 12/1989 | Forte |
| 5,007,933 A | 4/1991 | Sidebotham |
| 5,071,438 A | 12/1991 | Jones |
| 5,116,375 A | 5/1992 | Hofmann |
| 5,133,758 A | 7/1992 | Hollister |
| 5,147,405 A | 9/1992 | Van Zile |
| 5,219,362 A | 6/1993 | Tuke |
| 5,326,361 A | 7/1994 | Hollister |
| 5,330,533 A | 7/1994 | Walker |
| 5,344,460 A | 9/1994 | Turanyi |
| 5,358,527 A | 10/1994 | Forte |
| 5,370,699 A | 12/1994 | Hood |
| 5,387,240 A | 2/1995 | Pottenger |
| 5,395,401 A | 3/1995 | Bahler |
| 5,405,396 A | 4/1995 | Heldreth |
| 5,413,604 A | 5/1995 | Hodge |
| 5,549,686 A | 8/1996 | Johnson |
| 5,571,194 A | 11/1996 | Gabriel |
| 5,609,639 A | 3/1997 | Walker |
| 5,609,643 A | 3/1997 | Colleran |
| 5,639,279 A | 6/1997 | Burkinshaw |
| 5,658,342 A | 8/1997 | Draganich |
| 5,681,354 A | 10/1997 | Eckhoff |
| 5,683,468 A | 11/1997 | Pappas |
| 5,702,458 A | 12/1997 | Burstein |
| 5,702,466 A | 12/1997 | Pappas |
| 5,755,801 A | 5/1998 | Walker |
| 5,776,201 A | 7/1998 | Colleran |
| 5,778,537 A | 7/1998 | Leini |
| 5,800,552 A | 9/1998 | Forte |
| 5,811,543 A | 9/1998 | Hao |
| 5,824,100 A | 10/1998 | Kester |
| 5,824,102 A | 10/1998 | Buscayret |
| 5,871,543 A | 2/1999 | Hofmann |
| 5,871,546 A | 2/1999 | Colleran |
| 5,879,392 A | 3/1999 | McMinn |
| 5,906,643 A | 5/1999 | Walker |
| 5,935,173 A | 8/1999 | Roger |
| 5,964,808 A | 10/1999 | Blaha |
| 5,997,577 A | 12/1999 | Herrington |
| 6,004,351 A | 12/1999 | Tomita |
| 6,013,103 A | 1/2000 | Kaufman |
| 6,039,764 A | 3/2000 | Pottenger |
| 6,056,779 A | 5/2000 | Noyer |
| 6,080,195 A | 6/2000 | Colleran |
| 6,123,729 A | 9/2000 | Insall |
| 6,203,576 B1 | 3/2001 | Afriat |
| 6,206,926 B1 | 3/2001 | Pappas |
| 6,264,697 B1 | 7/2001 | Walker |
| 6,299,646 B1 | 10/2001 | Chambat |
| 6,325,828 B1 | 12/2001 | Dennis |
| 6,344,059 B1 | 2/2002 | Krakovits |
| 6,379,388 B1 | 4/2002 | Ensign |
| 6,443,991 B1 | 9/2002 | Running |
| 6,475,241 B2 | 11/2002 | Pappas |
| 6,491,726 B2 | 12/2002 | Pappas |
| 6,540,787 B2 | 4/2003 | Biegun |
| 6,558,426 B1 | 5/2003 | Masini |
| 6,582,469 B1 | 6/2003 | Tornier |
| 6,589,283 B1 | 7/2003 | Metzger |
| 6,699,291 B1 | 3/2004 | Augoyard |
| 6,730,128 B2 | 5/2004 | Burstein |
| 6,764,516 B2 | 7/2004 | Pappas |
| 6,770,099 B2 | 8/2004 | Andriacchi |
| 6,797,005 B2 | 9/2004 | Pappas |
| 6,840,905 B2 | 1/2005 | Gotschim |
| 6,846,329 B2 | 1/2005 | McMinn |
| 6,893,388 B2 | 5/2005 | Reising |
| 6,893,467 B1 | 5/2005 | Bercovy |
| 6,916,340 B2 | 7/2005 | Metzger |
| 6,926,738 B2 | 8/2005 | Wyss |
| 6,972,039 B2 | 12/2005 | Metzger |
| 6,986,791 B1 | 1/2006 | Metzger |
| 7,025,788 B2 | 4/2006 | Metzger |
| 7,066,963 B2 | 6/2006 | Naegerl |
| 7,081,137 B1 | 7/2006 | Servidio |
| 7,105,027 B2 | 9/2006 | Lipman |
| 7,160,330 B2 | 1/2007 | Axelson, Jr. |
| 7,261,740 B2 | 8/2007 | Tuttle |
| 7,326,252 B2 | 2/2008 | Otto |
| 7,422,605 B2 | 9/2008 | Burstein |
| 7,572,292 B2 | 8/2009 | Crabtree |
| 7,658,767 B2 | 2/2010 | Wyss |
| 7,678,152 B2 | 3/2010 | Suguro |
| 7,842,093 B2 | 11/2010 | Peters |
| 7,875,081 B2 | 1/2011 | Lipman |
| 8,915,965 B2 | 12/2014 | Komistek |
| 2003/0009232 A1 | 1/2003 | Metzger |
| 2003/0191533 A1* | 10/2003 | Dixon ............ A61L 27/04 623/17.14 |
| 2004/0243244 A1 | 12/2004 | Otto |
| 2004/0243245 A1 | 12/2004 | Plumet |
| 2005/0055102 A1* | 3/2005 | Tornier ............ A61F 2/389 623/20.32 |
| 2005/0096747 A1 | 5/2005 | Tuttle |
| 2005/0143832 A1 | 6/2005 | Carson |
| 2005/0154472 A1 | 7/2005 | Afriat |
| 2005/0209701 A1 | 9/2005 | Suguro |
| 2005/0209702 A1 | 9/2005 | Todd |
| 2006/0015185 A1 | 1/2006 | Chambat |
| 2006/0178749 A1 | 8/2006 | Pendleton |
| 2007/0135926 A1 | 6/2007 | Walker |
| 2008/0021566 A1 | 1/2008 | Peters |
| 2008/0243258 A1 | 10/2008 | Sancheti |
| 2008/0269596 A1 | 10/2008 | Revie |
| 2009/0043396 A1 | 2/2009 | Komistek |
| 2009/0306785 A1 | 12/2009 | Farrar |
| 2009/0319047 A1 | 12/2009 | Walker |
| 2009/0326663 A1 | 12/2009 | Dun |
| 2010/0016977 A1 | 1/2010 | Masini |
| 2010/0036500 A1 | 2/2010 | Heldreth |

FOREIGN PATENT DOCUMENTS

| | | |
|---|---|---|
| EP | 636352 B1 | 1/2002 |
| EP | 1440675 A1 | 7/2004 |
| EP | 1591082 B1 | 9/2009 |
| FR | 2417971 A1 | 2/1979 |
| FR | 2621243 A1 | 4/1989 |
| FR | 2787012 A1 | 6/2000 |
| FR | 2835178 A1 | 8/2003 |
| WO | WO 02009624 A1 | 2/2002 |
| WO | WO 04058108 A1 | 7/2004 |
| WO | WO 05072657 A1 | 8/2005 |

(56) References Cited

FOREIGN PATENT DOCUMENTS

| WO | WO 07108804 A1 | 9/2007 |
|---|---|---|
| WO | WO 07108933 A1 | 9/2007 |
| WO | WO 07119173 A1 | 10/2007 |

OTHER PUBLICATIONS

Asano et al. "In Vivo Three-Dimensional Knee Kinematics Using a Biplanar Image-Matching Technique," Clin Orthop Rel Res, 388: 157-166, (2001) (10 Pgs).

Barnes, C.L., et al, Kneeling is Safe for Patients Implanted With Medial-Pivot Total Knee Arthroplasty Designs, Journal of Arthroplasty, vol. 00, No. 0 (2010), 1-6, 6 Pgs.

Bertin et al., "In Vivo Determination of Posterior Femoral Rollback for Subjects Having a Nexgen Posterior Cruciate-Retaining Total Knee Arthroplasty," J Arthroplasty, vol. 17, No. 8, (2002), 9 Pages.

Blaha, et al., "Kinematics of the Human Knee Using an Open Chain Cadaver Model", Clinical Orthopaedics and Related Research, vol. 410 (2003); 25-34.

Clary et al., "Kinematics of Posterior Stabilized and Cruciate Retaining Knee Implants During an In Vitro Deep Knee Bend," 54th Annual Meeting of the Orthopaedic Research Society, Poster No. 1983, (Mar. 2008).

D'Lima et al., "Quadriceps Moment Arm and Quadriceps Forces After Total Knee Arthroplasty," Clin Orthop Rel Res 392:213-20, 2001.

Dennis, et al, "A Multi-Center Analysis of Axial Femorotibial Rotation After Total Knee Arthroplasty", Clinical Orthopaedics 428 (2004); 180-89.

Dennis, et al., "In Vivo Anteroposterior Femorotibial Translation of Total Knee Arthroplasty: A Multicenter Analysis," Clin Orthop Rel Res, 356: 47-57, (1998).

Dennis et al., "In Vivo Determination of Normal and Anterior Cruciate Ligament-Deficient Knee Kinematics," J Biomechanics, 38, 241-253, (2005), 13 Pgs.

Dennis et al "Multicenter Determination of In Vivo Kinematics After Total Knee Arthroplasty," Clin Orthop Rel Res., 416, 37-57, 21 Pgs (2003).

Fan, Cheng-Yu, et al, Primitive Results After Medial-Pivot Knee Arthroplasties: A Minimum 5-Year Follow-Up Study, The Journal of Arthroplasty, vol. 25, No. 3, 492-496, (2010) 5 Pgs.

Ferris, "Matching Observed Spiral Form Curves to Equations of Spirals in 2-D Images,"The First Japanese-Australian Joint Seminar, 7 Pgs (Mar. 2000).

Freeman, M.A.R., et al, The Movement of the Normal Tibio-Femoral Joint, The Journal of Biomechanics 38 (2005) (2), pp. 197-208, 12 Pgs.

Fuller, et al., "A Comparison of Lower-Extremity Skeletal Kinematics Measured Using Skin and Pin Mounted Markers", Human Movement Science 16 (1997) 219-242.

Goodfellow et al., "The Mechanics of the Knee and Prosthesis Design," The Journal of Bone and Joint Surgery, vol. 60-B, No. 3, 12 Pgs (Aug. 1978).

Hill, et al., "Tibiofemoral Movement 2: The Loaded and Unloaded Living Knee Studied by MRI", The Journal of Bone & Joint Surgery, vol. 82-B, No. 8 (Nov. 2000) 1196-1198.

P. Johal et al, "Tibio-Femoral Movement in the Living Knee. A Study of Weight Bearing and Non-Weight Bearing Knee Kinematics Using 'Interventional' MRI," Journal of Biomechanics, vol. 38, Issue 2, (Feb. 2005), pp. 269-276 (8 Pgs).

Karachalios, et al., "A Mid-Term Clinical Outcome Study of the Advance Medial Pivot Knee Arthroplasty," www.sciencedirect.com, The Knee 16 (5 Pgs) 484-488 (Accepted Mar. 9, 2009).

Kessler et al., "Sagital Curvature of Total Knee Replacements Predicts In Vivo Kinematics," Clinical Biomechanics 22(1): 52-58, (2007).

Komistek, et al., "In Vivo Fluoroscopic Analysis of the Normal Human Knee", Clinical Orthopaedics 410 (2003): 69-81.

Komistek, et al., "In Vivio Polyethylene Bearing Mobility is Maintained in Posterior Stabilized Total Knee Arthroplasty", Clinical Orthopaedics 428 (2004): 207-213.

Koo, et al., "The Knee Joint Center of Rotation is Predominantly on the Lateral Side During Normal Walking", Journal of Biomechanics, vol. 41 (2008); 1269-1273.

Li et al., "Anterior Cruciate Ligament Deficiency Alters the In Vivo Motion of the Tibiofemoral Cartilage Contact Points in Both Anteroposterior and Mediolateral Directions," JBJS-AM, vol. 88, No. 8, (Aug. 2006), 10 Pgs.

Mannan, et al., "The Medical Rotation Total Knee Replacement: A Clinical and Radiological Review at a Mean Follow-Up of Six Years", The Journal of Bone and Joint Surgery, vol. 91-B, No. 6 (Jun. 2009): 750-756.

Moonot, et al., "Correlation Between the Oxford Knee and American Knee Society Scores at Mid-Term Folow-Up", The Journal of Knee Surgery, vol. 22, No. 3 (Jul. 2009), 226-230.

Murphy, Michael Charles, "Geometry and the Kinematics of the Normal Human Knee", Submitted to Massachusetts Institute of Technology (1990).

Nakagawa, et al., "Tibiofemoral Movement 3: Full Flexion in the Living Knee Studied by MRI", The Journal of Bone and Joint Surgery, vol. 82-B, No. 8 (Nov. 2000): 1199-1200.

"Nexgen Complete Knee Solution Cruciate Retaining Knee (CR)," Zimmer, Available at: http:--zimmer.com.au-ctl?template=PC&op=global&action=&template=PC&id=356, (downloaded on Feb. 18, 2009), (1 page).

Omori, et al., "The Effect of Geometry of the Tibial Polyethylene Insert on the Tibiofemoral Contact Kinematics in Advance Medical Pivot Total Knee Arthroplasty", The Journal of Orthopaedics Science (2009) 14: 754-760.

Ranawat, "Design May Be Counterproductive for Optimizing Flexion After TKR," Clin Orthop Rel Res 416: 174-6, (2003).

Ries, "Effect of ACL Sacrifice, Retention or Substitution on K After TKA," http:--www.orthosupersite.com-view.asp?rid=23134, (Aug. 2007), 5 Pgs.

Saari et al., "The Effect of Tibial Insert Design on Rising From a Chair, Motion Analysis After Total Knee Replacement," Clin Biomech 19; 951-6, (2004).

Scorpio Knee TS Single Axis Revision Knee System, Stryker Orthopaedics retrieved from http:--www.stryker.com-stellent-groups-public-documents-web_prod-023609,pdf (6 pgs), Literature No. LSKTS-B (2004).

Shakespeare, et al., "Flexion After Total Knee Replacement. A Comparison Between the Medial Pivot Knee and a Posterior Stabilised Implant," www.sciencedirect.com, The Knee 13 (2006): 371-372.

Suggs et al., "Three-Dimensional Tibiofemoral Articular Contact Kinematics of a Cruciate-Retaining Total Knee Arthroplasty," JBJS-AM, vol. 88, No. 2, (2006), 9 Pgs.

Uvehammer et al., "In Vivo Kinematics of Total Knee Arthroplasty: Concave Versus Posterior-Stabilised Tibial Joint Surface," J Orthop Res vol. 82-B, No. 4 (May 2000) 10 Pages.

Uvehammer et al., "In Vivo Kinematics of Total Knee Arthroplasty: Flat Compared With Concave Tibial Joint Surface," J Orthop Res 18(6): 856-64, 2000.

"Vanguard Complete Knee System," Biomet, Available at Http:--www.biomet.com-patients-vanguard_complete.cfm, (downloaded on Feb. 2009), 3 pgs.

Walker, et al., "Motion of a Mobile Bearing Knee Allowing Translation and Rotation", Journal of Arthroplasty 17 (2002): 11-19.

Wang et al., "A Biomechanical Comparison Between the Single-Axis and Multi-Axis Total Knee Arthroplasty Systems for Stand-to-Sit Movement," Clin Biomech 20(4); 428-33, (2005).

Wang et al., "Biomechanical Differences Exhibited During Sit-to-Stand Between Total Knee Arthroplasty Designs of Varying Radii," J Arthroplasty 21(8): 1196-9, (2006).

Yoshiya et al., "In Vivo Kinematic Comparison of Posterior Cruciate-Retaining and Posterior-Stabilized Total Knee Arthroplasties Under Passive and Weight-Bearing Conditions," J Arthroplasty, vol. 20, No. 6, 7 Pgs (2005).

Kurosawa, et al., "Geometry and Motion of the Knee for Implant and Orthotic Design", The Journal of Biomechanics 18, pp. 487-499, 12 pages (1985).

(56) References Cited

OTHER PUBLICATIONS

Shaw et al, "The Longitudinal Axis of the Knee & the Role of the Cruciate Ligaments", J. Bone Joint Surg. Am;56:1603-1609 (1974).
PCT Notification Concerning Transmittal of International Prel. Report for Corresponding International App. No. PCT-US2006-010431, dated Jun. 5, 2007, 8 Pages.
PCT Notification Concerning Transmittal of International Prel. Report for Corresponding International App. No. PCT-US2006-010431, dated Oct. 2, 2008, 6 Pages.
European Search Report for App. 09164478.1-2310 dated Oct. 20, 2009.
Australian Search Report for Corresponding App.. No. 2006340364, dated Dec. 11, 2009, 2 Pages.
European Search Report for EPO App No. 09164228.0/1526, dated Feb. 2, 2010, 6 Pgs.
European Search Report From Corresponding EPO App No. 06739287.8 dated Mar. 16, 2010, 3 Pages.
European Search Report for App. 09164478.1-2310/2145605 dated Apr. 28, 2010.
European Search Report in Corresponding EPO App No. 10162138.1 dated Aug. 30, 2010, 7 Pages.
Japanese SR for Corresponding Patent Application No. 2009-501393, dated Oct. 26, 2010, 5 Pages.
European Search Report for EPO App No. 10174440.7-1526, dated Dec. 10, 2010, 4 Pgs.
European Search Report for EPO App No. 10174439.9-1526, dated Dec. 20, 2010, 4 Pgs.
European Search Report From Corresponding EPO App. No. 12164381.1-2310, dated May 18, 2012, 4 Pages.
European Search Report in Corresponding EPO App. No. 12181217.6-2310, dated Jan. 15, 2013, 7 Pages.
European Search Report From Corresponding EPO Patent App No. 12164381.1-1654, dated Mar. 7, 2013, 3 Pages.

\* cited by examiner

MOMENT INDUCED TOTAL ARTHROPLASTY PROSTHETIC

CROSS REFERENCE TO RELATED APPLICATIONS

This application is a continuation of U.S. patent application Ser. No. 14/963,293, which is a divisional of U.S. patent application Ser. No. 14/132,343, now U.S. Pat. No. 9,254,197, which is a divisional of U.S. patent application Ser. No. 12/203,987, now U.S. Pat. No. 8,636,807, which is a continuation that claims priority under 35 U.S.C. § 120 to Patent Cooperation Treaty Application Serial No. PCT/US2006/010431 filed on Mar. 21, 2006, entitled "MOMENT INDUCED TOTAL ARTHROPLASTY PROSTHETIC," the disclosures and amended disclosure of which are hereby incorporated by reference in their entireties.

RELATED ART

Field of the Invention

The exemplary embodiments disclosed herein are directed to implanted prosthetic devices and, more specifically, to implanted prosthetic joints that simulate the natural biomechanics of native mammalian joints. Further exemplary embodiments also encompass methods of inducing moments within an implanted prosthetic joint, as well as implanted prosthetic devices that incorporate induced moments.

Brief Discussion of Related Art

Previous research studies have documented that the amount of rotation occurring in the knee, during walking and high flexion activities, varies greatly between a natural knee (no prior surgeries and no history of clinical abnormalities) and a surgically revised knee such as those having undergone total knee arthroplasty (TKA). The axial femorotibial rotational pattern of the femur relative to the tibia during flexion of a natural knee induces tibia internal rotation relative to the femur, and tibia external rotation relative to the femur as the knee extends. This internal rotational mechanism results in part from the length and tension within the cruciate and collateral ligaments and anatomic variances in dimensions of the medial and lateral femoral and tibial condyles.

The exact axial femorotibial rotational pattern after TKA is less clear, but has been shown to vary considerably. Many have hypothesized that decreases in axial rotation after TKA may be related to removal or alteration of the cruciate ligaments and/or failure to exactly duplicate geometry of the medial and lateral femoral and tibial condyles, although most hypothesize that this reduced motion derives from the inability to reproduce correct condylar geometries.

A multicenter, in vivo, weight-bearing kinematic analysis has demonstrated similar average axial rotational values in fixed versus mobile bearing TKA prosthetics. Controversy exists, however, as to the exact site of axial rotation (superior vs. inferior aspect of the tibial insert) in mobile bearing TKA prosthetics. Many fixed and mobile bearing TKA prosthetics have demonstrated significantly reduced axial rotation, while others have documented that TKA patients often experience a reverse rotation pattern, where the tibia externally rotates about the femur with increasing knee flexion.

INTRODUCTION TO THE INVENTION

The exemplary embodiments disclosed herein are directed to implantable prosthetic devices simulating the natural biomechanics of native mammalian joints. These exemplary embodiments induce moments within an implantable prosthetic joint to impart rotational movement between joint components. The exemplary embodiments also encompass the joint components themselves that induce moments, as well as methods for inducing moments to impart rotation between complimentary prosthetic components within an implantable joint.

In one aspect, the present invention provides a prosthetic knee implant system comprising a distal femoral component, a tibial tray and a mobile bearing tibial tray insert. The mobile bearing tibial tray insert is rotatably mountable on the tibial tray for articulation with the distal femoral implant component. The distal femoral implant component has a medial condyle and a lateral condyle and the mobile bearing tibial tray insert has a medial condyle receiver spaced apart from a lateral condyle receiver. The mobile bearing tibial tray insert rotates with respect to the tibial tray around a substantially vertical first rotational axis offset laterally from the medial-lateral centerline of the mobile bearing tibial tray insert and the distal femoral implant component rotates with respect to the tibial tray insert about a substantially vertical second rotational axis offset medially from the first rotational axis.

In a more detailed embodiment, the first rotational axis is offset laterally from a medial-lateral centerline of the mobile bearing tibial tray insert.

In another more detailed embodiment, the first rotational axis is offset anteriorly from an anterior-posterior centerline of the mobile bearing tibial tray insert. Alternatively, the first rotational axis may be offset posteriorly from an anterior-posterior centerline of the mobile bearing tibial tray insert.

In another more detailed embodiment, the lateral condyle receiver includes at least one of a convex shape or a sequentially sloped from anterior to posterior shape and the medial condyle receiver includes a concave shape.

In another more detailed embodiment, the mobile bearing tibial tray insert includes a recess adapted to receive a projection from the tibial tray allowing the mobile bearing tibial tray insert to rotate with respect to the tibial tray about the first rotational axis. Alternatively, the mobile bearing tibial tray insert may include a projection adapted to be received by a recess within the tibial tray allowing the mobile bearing tibial tray insert to rotate with respect to the tibial tray about the first rotational axis In another more detailed embodiment, there is translational laxity between the medial condyle receiver and the medial condyle during flexion of the knee.

In another more detailed embodiment, the medial condyle receiver and the medial condyle are shaped to have up to 12.5 mm of translational laxity at greater than 20 degrees of knee flexion.

In another more detailed embodiment, the medial condyle is larger than the lateral condyle.

BRIEF DESCRIPTION OF THE DRAWINGS

FIGS. 14(a) & (b) are pictorial profile representations of an exemplary MITKA posterior cruciate retaining TKA having increased conformity between the medial condyle and the medial receiver of the tibial insert at varying degrees of knee flexion;

FIGS. 14(c) & (d) are pictorial profile representations of an exemplary MITKA posterior cruciate retaining TKA having an increased sloped between the lateral condyle and the tibial insert at varying degrees of knee flexion;

FIGS. 14(e) & (f) are pictorial profile representations of an exemplary MITKA posterior cruciate retaining TKA with a lateral convex shape along which the lateral condyle rides at varying degrees of knee flexion;

DETAILED DESCRIPTION

The exemplary embodiments described and illustrated below encompass methods of inducing moments within an implanted prosthetic joint, as well as implantable prosthetic joints and components thereof inducing moments. Of course, it will be apparent to those of ordinary skill in the art that the embodiments discussed below are exemplary in nature and may be reconfigured without departing from the scope and spirit of the invention. However, for clarity and precision, the exemplary embodiments as discussed below may include optional steps, methods, and features that one of ordinary skill should recognize as not being a requisite to fall within the scope of the claims.

Basic principals governing the laws of mechanics are taken from Newton's Laws: (A) every object in a state of uniform motion tends to remain in that state of motion unless an external force is applied to it; (B) the relationship between an object's mass m, its acceleration a, and the applied force F, is F=ma; and, (C) for every action there is an equal and opposite reaction. The above laws of mechanics pertain to external forces applied to a system, however, when an in-plane force is applied to an object that has the ability to move, and if the applied force is greater than the resistive force (gravity, friction, etc.), the object will begin to move. Throughout knee flexion, whether during gait or into deep flexion, the cruciate ligaments of a natural knee force the tibia to internally rotate, levering the femur with respect to the tibia. It has been documented that the absence of the cruciate ligaments leads to a decrease in axial rotation.

For total knee arthroplasty (TKA) prosthetics, three primary forces may be exerted thereupon: (1) applied forces, which are produced by muscles passing across the knee joint; (2) bearing surface contact forces occurring between the femur and the tibia at the contact points and between the femur and the patella at the contact points; and, (3) constraint forces produced by ligaments resisting the active forces. However, the incidence and magnitude patterns of normal axial rotation of a knee prosthesis is governed by, and can only be induced to rotate by introducing moment arms with respect to active forces to cause rotation. In an exemplary system, a vector V has a distance D, with a line of action passing through a starting point P of the vector V. The moment M of the vector V about point P is characterized by Equation #1: M=R×V; where R is the position vector from point P to a second point along the vector V.

Before a moment analysis can be conducted for any TKA prosthetic, an understanding of the forces acting on the knee, both magnitude and direction, should be clearly determined and understood. The most effective method for deriving muscle, bearing surface and ligament forces, simultaneously, is through mathematical modeling techniques. It has been demonstrated that, with a proper understanding of knee mechanics, it is possible to derive equations to determine in vivo forces. Although it is important to know the magnitude of the forces applied at the knee, it is equally important to determine the direction of those applied forces. Proper direction of contact forces acting at the femorotibial and patellofemoral interfaces will ensure proper summation of the moments about a chosen point. Therefore, it is important to determine the direction of the velocity of the point on the femur, point FT, in contact with the tibia, which will allow for the determination of the direction of the bearing surface contact force occurring between points FT and TF, which is the point on the tibia in contact with the femur.

In a natural knee, like any mechanical system that has any two objects in contact, three possible conditions could occur, which lead to vastly different conditions at the contact point between the two objects. These three conditions are: (1) pure rolling; (2) pure slipping; and, (3) a combination of rolling and slipping.

Figure 1:
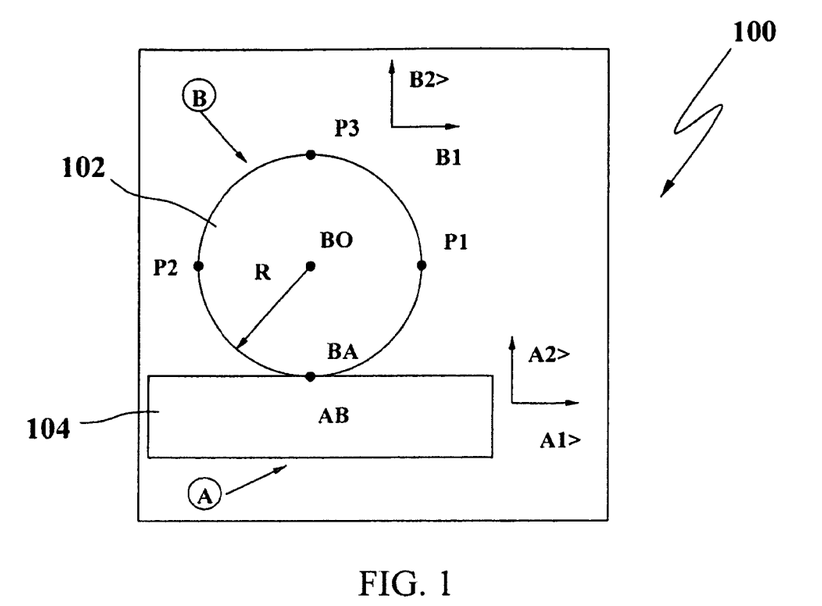
FIG. 1 is a free body diagram of a cylinder, B, contacting a platform, A.

Referencing FIG. 1, an exemplary free-body diagram 100 includes a round cylinder (Body A) 102 with radius R moving with respect to a generally planar platform (Body B) 104 that is fixed in the Newtonian reference frame. In this simple example, two reference frames are defined for each object 102, 104, where the "A2>" and "B2>" directions are opposite of gravity. The point of contact between the objects 102, 104 is mutually defined by two points: point AB on the platform 104, and point BA on the cylinder 102. Three other points P1, P2, P3 are equidistantly spaced around the circumference of the cylinder 102, with the longitudinal center being identified by point BO. Point P1 is spaced a distance R in the A1> direction and a distance R in the A2> direction from point BA. Point P2 is spaced from point BA a distances R in the −A1> direction and R in the A2> direction. Point P3 is spaced a distance 2R in the A2> direction, from point BA.

Under pure rolling conditions, we can assume the velocity vector V_BO_A>=A1>, where: the radius R=1; and, the angular velocity of the cylinder ω, relative to the reference frame for the platform around the A3> axis, is equal to −A3>. One can then determine the velocity for points P1, P2, P3 and BO, which are determined using Equations #2-#5:

$$V\_P1\_A{>}{=}V\_BO\_A{>}{+}\omega\_B\_A{>}{\times}P\_BO\_P1{>}$$

$$V\_P1\_A{>}{=}A1{>}{+}{-}A3{>}x\,A1{>}$$

$$V\_P1\_A{>}{=}A1{>}{-}A2{>} \quad \text{Equation \#2:}$$

$$V\_BA\_A{>}{=}V\_BO\_A{>}{+}\omega\_B\_A{>}{\times}P\_BO\_BA{>}$$

$$V\_BA\_A{>}{=}A1{>}{+}{-}A3{>}{\times}{-}A2{>}$$

$$V\_BA\_A{>}{=}A1{>}{-}A1{>}{=}0{>} \quad \text{Equation \#3:}$$

$$V\_P2\_A{>}{=}A1{>}{+}A2{>} \quad \text{Equation \#4:}$$

$$V\_P3\_A{>}{=}2{\cdot}A1{>} \quad \text{Equation \#5:}$$

Therefore, under pure rolling conditions, the velocity of point BA must equal the velocity of point AB. Since the platform 104 is "fixed" and not moving in the Newtonian reference frame, all points on the platform have a velocity equal to zero. This simple analysis shows that the velocity of point BA, on the cylinder 102, is equal to zero, under pure rolling conditions.

Under pure slipping conditions, the velocities for this same system, shown in FIG. 1, are different for each point along the cylinder 102. A practical way to describe pure slipping would be a car on ice. If the friction coefficient were equal to zero, the tires would spin, but the car would remain stationary. Therefore, in the knee, under pure slipping the V_BO_A>=0>, and similar to our example shown in FIG. 1, the Radius=1, ω=−A3>. Then the velocities for points BA, P1, P2, and P3 are determined using Equations #6-#9:

$$V\_P1\_A{>}{=}V\_BO\_A{>}{+}\omega\_B\_A{>}{\times}P\_BO\_P1{>}$$

$$V\_P1\_A{>}{=}0{>}{+}{-}A3{>}{\times}A1{>}$$

$$V\_P1\_A{>}{=}{-}A2{>} \quad \text{Equation \#6:}$$

$$V\_BA\_A{>}{=}V\_BO\_A{>}{+}\omega\_B\_A{>}{\times}P\_BO\_BA{>}$$

$$V\_BA\_A{>}{=}0{>}{+}{-}A3{>}{\times}{-}A2{>}$$

$$V\_BA\_A{>}{=}{-}A1{>} \quad \text{Equation \#7:}$$

$$V\_P2\_A{>}{=}A2{>} \quad \text{Equation \#8:}$$

$$V\_P3\_A{>}{=}A1{>} \quad \text{Equation \#9:}$$

Therefore, under pure slipping, the velocity of point BA is equal to −A1>, and the direction of the velocity is opposite in direction to posterior femoral rollback of the femoral condyles in a knee. Although it has been assumed that the velocity vector of the contact point between the femoral condyles and the tibial plateau would be in the posterior direction, under pure slipping, the correct direction of the velocity vector is in the anterior direction during flexion and in the posterior direction during extension. Although pure rolling and pure slipping have been described, it can be assumed that, under in vivo conditions, "only" pure rolling or "only" pure slipping conditions cannot occur.

Figure 2:
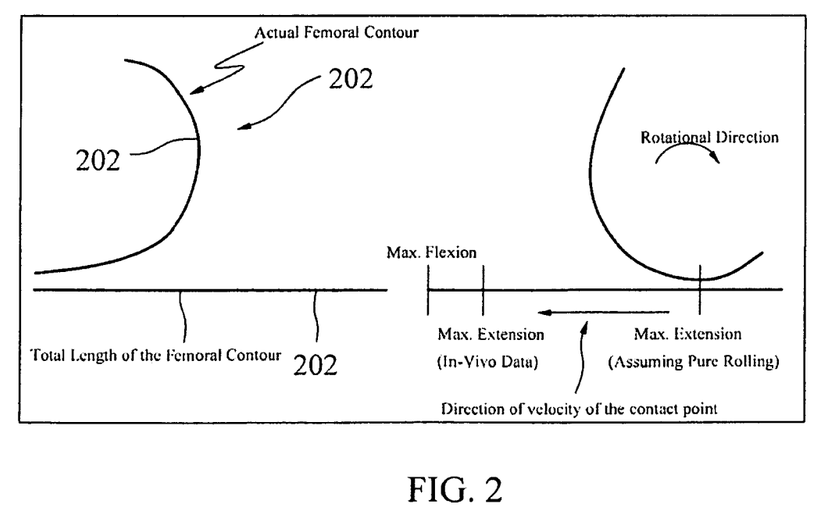
FIG. 2 is a diagram representing the curvature of a femoral condyle as a linear segment and showing the amount of the linear segment correspondingly contacted during flexion of the knee joint.

Referencing FIG. 2, a circumferential distance 200 of a prosthetic femoral condyle 202 can be represented by a flat line 204. Under pure rolling conditions, the prosthetic femoral condyle 202 would follow the flat line 204 path, which is much greater in distance than an anterior/posterior dimension of a prosthetic tibial insert (not shown). Previous analyses have documented that the amount of anterior posterior motion for a natural knee can range between 10 to 25 mm for the lateral condyle and, for a TKA prosthetic, this motion could be 10 mm in the anterior direction or 15 mm posterior. Thus, in a TKA prosthesis, the most dominant motion occurring at the contact point between the femoral condyle 202 and the tibial insert is slipping.

Referring again to FIG. 1, an analysis can be conducted to determine the velocities on the cylinder 102 at the bearing surface interface BA, AB when both slipping and rolling are present. In this analysis, we can assume V_BO_A>=A1>, radius R=1, and the angular velocity of the cylinder ω=−2A3>. Therefore, the velocities for points P1, P2, P3 and BA can be determined using Equations #10-#13:

$$V\_P1\_A{>}{=}V\_BO\_A{>}{+}\omega\_B\_A{>}{\times}P\_BO\_P1{>}$$

$$V\_P1\_A{>}{=}A1{>}{+}{-}2A3{>}{\times}A1{>}$$

$$V\_P1\_A{>}{=}A1{>}{-}2A2{>} \quad \text{Equation \#10:}$$

$$V\_BA\_A{>}{=}V\_BO\_A{>}{+}\omega\_B\_A{>}{\times}P\_BO\_BA{>}$$

$$V\_BA\_A{>}{=}A1{>}{+}{-}2A3{>}{\times}{-}A2{>}$$

$$V\_BA\_A{>}{=}A1{>}{-}2A1{>}{=}{-}A1{>} \quad \text{Equation \#11:}$$

$$V\_P2\_A{>}{=}A1{>}{+}2A2{>} \quad \text{Equation \#12:}$$

$$V\_P3\_A{>}{=}A1{>}{+}2A2{>}{=}3A2{>} \quad \text{Equation \#13:}$$

Under all three conditions (slipping, rolling, or a combination), an important piece of information is the velocity of point BA. During pure rolling, the velocity of point BA is equal to zero, but under pure slipping and a combination of rolling and slipping, in our examples, this velocity is not equal to zero. Under pure slipping the direction of the velocity BA is in the −A1> direction, opposite of the direction of posterior femoral rollback of the femoral condyles. During a combination of rolling and slipping, the direction of this velocity vector, V_BA_N>, in our example is in the −A1>, which is, again, in the opposite direction of contact point BA on AB. The magnitude of V_BA_N> can change, depending on the velocity of BO and the angular velocity of body B in the Newtonian reference frame, but the magnitude will always be in the −A1> direction. Therefore, it is disadvantageous to design a total knee arthroplasty prosthesis assuming that the forces at point BA on AB during knee flexion are in the A1> (posterior direction) direction. Instead, one should design a total knee arthroplasty prosthesis with the forces being applied in the −A1> direction (anterior direction) during knee flexion and in the A1> direction during knee extension, similar to the direction of velocity vector acting at this point. Also, it should be noted, that during flexion the velocity of the contact point BA is equal to zero, under pure rolling and is in the anterior direction (−A1>) under pure slipping. Therefore, during knee flexion, V_BA_N> is not in the posterior direction.

At present, all known TKA prosthetics are designed for equal distribution of forces at the contact points between the femoral components and the tibial components. Therefore, these TKA prosthetics do not incorporate moments to create axial rotation. During surgery, the goal of the surgeon is to create equal tension gaps between the femoral condyles and the tibial insert/plateau. If the amount of force acting between the medial condyle and the tibial insert is equal to the force acting between the lateral condyle and the tibial insert, it could be expected that the femoral components will not achieve axial rotation relative to the tibial insert because the medial and lateral condyle distances from the center of the tibial insert are also the same. If two forces act on a system and both forces are equal in magnitude and the moment arms to those forces, from a fixed point, are equal, then the moment of this system would be equal to zero.

Figure 3:
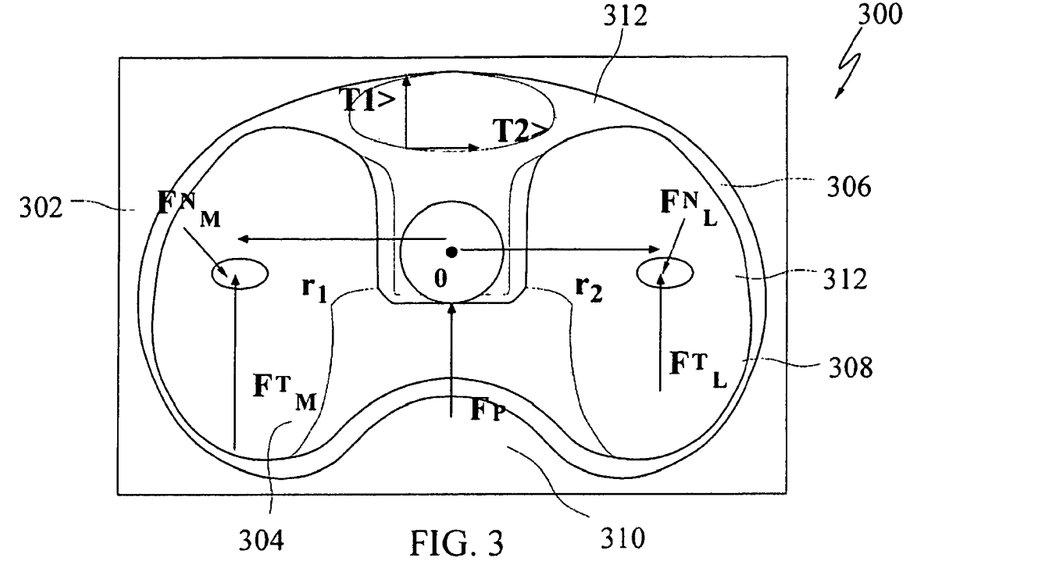
FIG. 3 is an overhead view of a prior art posterior stabilized mobile bearing total knee arthroplasty prosthetic insert having the polyethylene post aligned over the center of rotation.

Referencing FIG. 3, a typical posterior stabilized mobile bearing TKA prosthetic 300 accommodates five main contact forces: (1) the medial condyle force 302 in the vertical direction ($F^N_M$); (2) the medial condyle force 304 in the anterior/posterior direction ($F^T_M$); (3) the lateral condyle force 306 in the vertical direction ($F^N_L$); (4) the lateral condyle force 308 in the anterior/posterior direction ($F^T_L$); and (5) the force 310 applied by the cam on the post ($F_P$). Point O represents the rotation point of the polyethylene insert 312 relative to the tibial implant (not shown) about which moments are summated. Also included is the distance $r_1$ between point O to the medial condyle contact force, and the distance $r_2$ between point O to the lateral condyle.

If the moments are summated for the mobile bearing TKA prosthetic 300, around point O, in the T3> direction (perpendicular to the T1> and T2> directions), the moment equation is represented by Equation #14:

$$\Sigma M_o \cdot T3 \mathord{>} = I \cdot \alpha \cdot T3\mathord{>} \quad \text{Equation \#14:}$$

We can assume that the angular acceleration (α) of the polyethylene insert 312 relative to the tibial implant component in the T3> direction is negligible, and can be set equal to zero. Therefore, with this presumption in place, Equation #14 can be refined into Equation #15:

$$\Sigma M_o = 0 \text{ in the } T3\mathord{>} \text{ direction.}$$

$$\Sigma M_o \cdot T3\mathord{>} = -r_1 \cdot T2\mathord{>} \times F^T_M \cdot T1\mathord{>} + r_2 \cdot T2\mathord{>} \times F^T_L \cdot T1\mathord{>}, \quad \text{Equation \#15:}$$

Where the following information is known, the distance $r_1 = r_2 = r$, and the forces $F_M = F_L = F$, Equation #15 can be further simplified into Equation #16:

$$\Sigma M_o \cdot T3\mathord{>} = -rF \cdot (-T3\mathord{>}) + rF \cdot (-T3\mathord{>}),$$

$$\Sigma M_o \cdot T3\mathord{>} = 0. \quad \text{Equation \#16:}$$

As shown by Equation #16, if the distances $r_1$, $r_2$ from the rotation point O of a mobile bearing TKA prosthetic 300 are the same to the medial and lateral condyles, the sum of the moments is equal to zero. Thus, the polyethylene insert 312 does not rotate about the tibial component. An in vivo analysis of the mobile bearing TKA prosthesis 300 evidenced that 7/9 subjects experienced less than 2.0 degrees of axial rotation.

Figure 4:
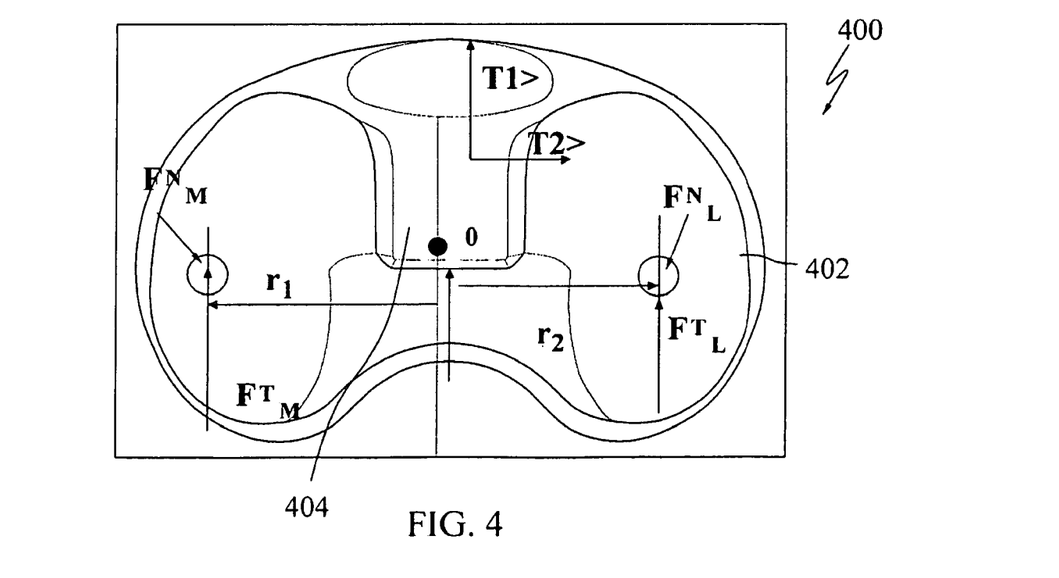
FIG. 4 is an overhead view of a prior art fixed bearing posterior stabilized total knee arthroplasty prosthetic insert having the polyethylene post located along the medial-lateral midline of the polyethylene insert.

Referring to FIG. 4, a typical fixed bearing TKA prosthetic 400 includes a tibial insert 402 (typically polyethylene) mounted to a tibial implant component (typically a metallic tibial tray, which is not shown). Unlike the mobile bearing posterior stabilized TKA prosthetic 300 of FIG. 3, the tibial insert 402 is fixed to the tibial implant component so that the insert does not rotate with respect to the tibial implant component. The forces acting on the fixed bearing posterior stabilized insert 402 are similar to those forces defined for the mobile bearing posterior stabilized TKA prosthetic 300 of FIG. 3.

Summation of moments acting on the fixed bearing polyethylene insert 402 can be conducted around the defined point O. The primary difference between the point O of FIG. 4, and point O of FIG. 3, is that the chosen point O does not represent a rotation point in FIG. 4, but rather a fixed physical point on the tibial insert 402 in the center of the post in the T2> direction. Summating the moments around point O is represented by Equation #14:

$$\Sigma M_o \cdot T3\mathord{>} = I \cdot \alpha \cdot T3\mathord{>} \quad \text{Equation \#14:}$$

Similar to the mobile bearing TKA prosthetic 300 of FIG. 3, we can assume that the angular acceleration (α) of the femur relative to the tibial insert 402 in the T3> direction is small, and can be set equal to zero. Therefore, with this presumption in place, Equation #14 can be refined into Equation #15:

$$\Sigma M_o = 0 \text{ in the } T3\mathord{>} \text{ direction.}$$

$$\Sigma M_o \cdot T3\mathord{>} = -r_1 \cdot T2\mathord{>} \times F^T_M \cdot T1\mathord{>} + r_2 \cdot T2\mathord{>} \times F^T_L \cdot T1\mathord{>}, \quad \text{Equation \#15:}$$

Where the following information is known, the distance $r_1 = r_2 = r$, and the forces $F_M = F_L = F$, Equation #15 can be further simplified into Equation #16:

$$\Sigma M_o \cdot T3\mathord{>} = -rF \cdot (-T3\mathord{>}) + rF \cdot (-T3\mathord{>})$$

$$\Sigma M_o \cdot T3\mathord{>} = 0 \quad \text{Equation \#16:}$$

If the polyethylene post 404 is located in the center of the tibial insert 402, in the T1> and T2> directions, then the sum of the moments, in the T3> direction, for the contact forces applied by the femoral component on the tibial insert is equal to zero. Previous in vivo analyses of TKA prosthetics have determined that all TKA prosthetics achieve less axial rotation than a natural knee, while a significant number of TKA recipients are able to achieve less than two degrees of axial rotation of the resulting knee joint and approximately ⅓ of these recipients experience a reverse axial rotation pattern, opposite that of a natural knee.

Figure 5:
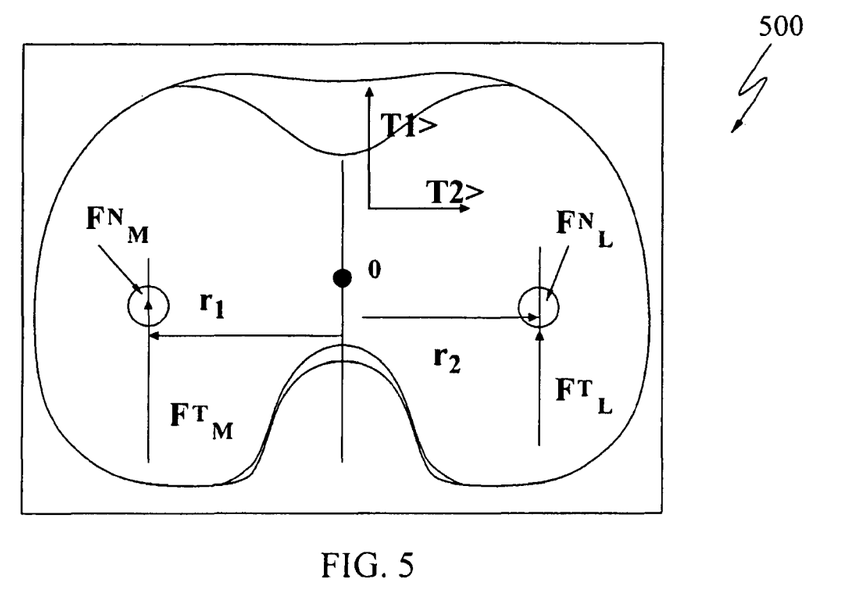
FIG. 5 is an overhead view of a prior art posterior cruciate retaining total knee arthroplasty prosthetic insert.

Referencing FIG. 5, a posterior cruciate retaining TKA prosthetic 500 (whether mobile or fixed bearing) allows for posterior cruciate ligament retention, without the presence of a cam/post mechanism 404 found in the posterior stabilized TKA prosthetic 400 of FIG. 4. The absence of the cam/post mechanism in a posterior cruciate retaining TKA prosthetic 500 leads to an analysis very similar to those for a posterior stabilized TKA prosthetics discussed above. Since the cam/post mechanism for present day posterior stabilized TKA prosthetics is in the center of the tibial insert, the cam/post force does not exert a moment. Therefore, when the cam/post mechanism does not induce rotation, the moment analysis for a mobile bearing posterior cruciate TKA prosthetic 500 will be similar to the moment analysis of a mobile bearing posterior stabilized TKA prosthetic 300 (see FIG. 3), and the moment analysis for a fixed bearing posterior cruciate retaining TKA prosthetic 500 will be similar to a fixed bearing posterior stabilized TKA prosthetic 400 (see FIG. 4), except for the resistive force of the posterior cruciate ligament. In other words, the sum of the moments for the contact forces applied by the femoral component on the tibial insert is equal to zero for these posterior cruciate retaining TKA prosthetics 500.

Figure 6:
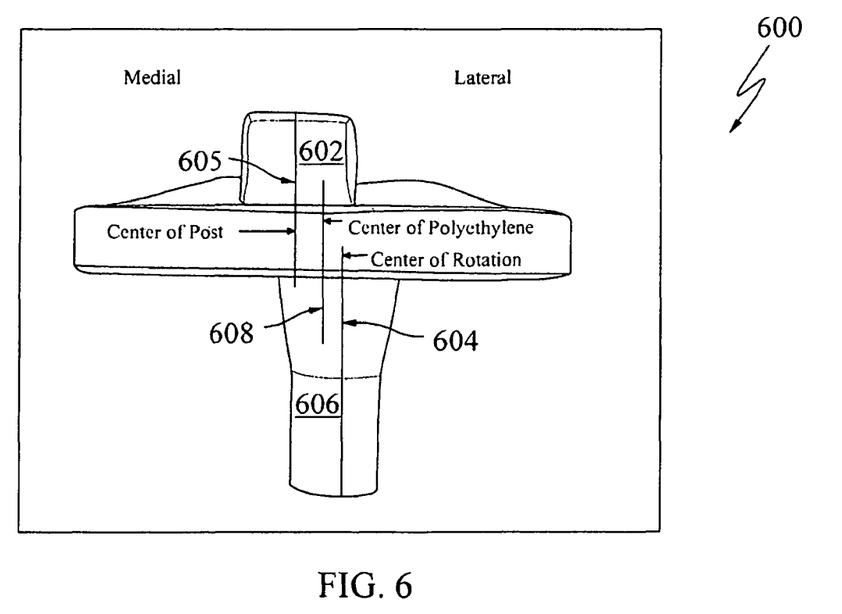
FIG. 6 is a rear, profile view of a first exemplary moment induced mobile bearing posterior stabilized total knee arthroplasty prosthetic in accordance with the present invention.

Referencing FIG. 6, an exemplary posterior stabilized mobile bearing Moment Induced Total Knee Arthroplasty (MITKA) prosthetic insert 600 is mounted to a prosthetic tibial stem 606, which is preferably implanted into a patient's tibia (not shown). The insert 600 includes a post 602 offset in the medial direction from the medial-lateral midline 608 of the insert 600 providing an axis of rotation 605 between the insert and a femoral component (not shown), and an axis of rotation 604 between the tibial stem 606 and the insert 600 that is shifted in the lateral direction from the medial-lateral midline 608.

Figure 7:
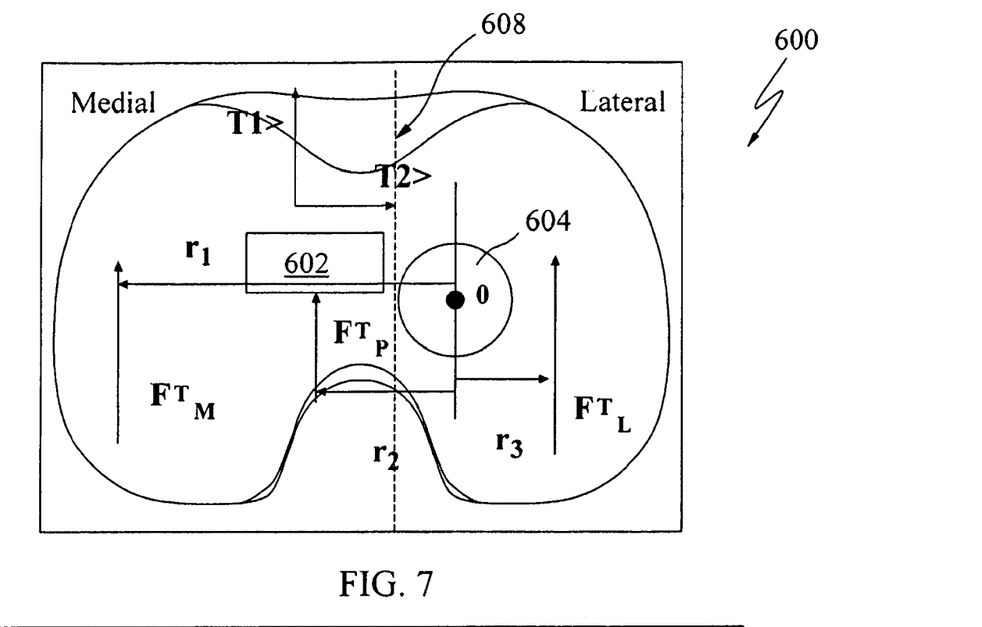
FIG. 7 is an overhead view of a first exemplary moment induced mobile bearing posterior stabilized total knee arthroplasty prosthetic insert in accordance with the present invention.

Referring to FIG. 7, a moment analysis of the exemplary MITKA prosthetic insert 600 includes summating the moments, around the point of rotation, O, in the T3> direction. The moment equation is represented by Equation #17:

$$\Sigma M_o \cdot T3 >= -r_1 \cdot T2 > \times F^T_M \cdot T1 > -r_3 \cdot T2 > \times F_P \cdot T1 > + r_2 \cdot T2 > \times F^T_L \cdot T1 > \quad \text{Equation \#17:}$$

Where the following information is known, the distance $r_1 = 2r$, $r_2 = r_3 = r$, and the forces $F^T_M = F^T_L = F_P = F$, Equation #17 can be further simplified into Equation #18:

$$\Sigma M_o \cdot T3 >= -2rF \cdot (-T3>) - rF \cdot (-T3>) + rF \cdot (-T3>)$$

$$\Sigma M_o \cdot T3 >= 2rF \cdot T3 > + rF \cdot T3 > - rF \cdot T3 >$$

$$\Sigma M_o \cdot T3 >= 2rF \cdot T3 > \quad \text{Equation \#18:}$$

In this exemplary moment summation, the moment induced by the exemplary MITKA prosthetic insert 600 is equal to 2rF, in the clockwise direction (looking down), leading to normal axial rotation of the tibial insert.

Unlike present day mobile bearing posterior stabilized TKA prosthetics 300 (see FIG. 3, for example), the tibial insert 600 for the MITKA knee will rotate in the clockwise direction (looking down) as a result of creating a distance between the rotation point O to the post 602 of the tibial insert 600 (distance represented by $r_3$), increasing the distance from the rotation point O to the medial condyle contact force $F^T_M$ (distance represented by $r_1$), and decreasing the distance from the rotation point O to the lateral condyle contact force $F^T_L$ (distance represented by $r_2$), allowing for the lateral condyle to move more posterior, similar to a natural knee.

Figure 8:
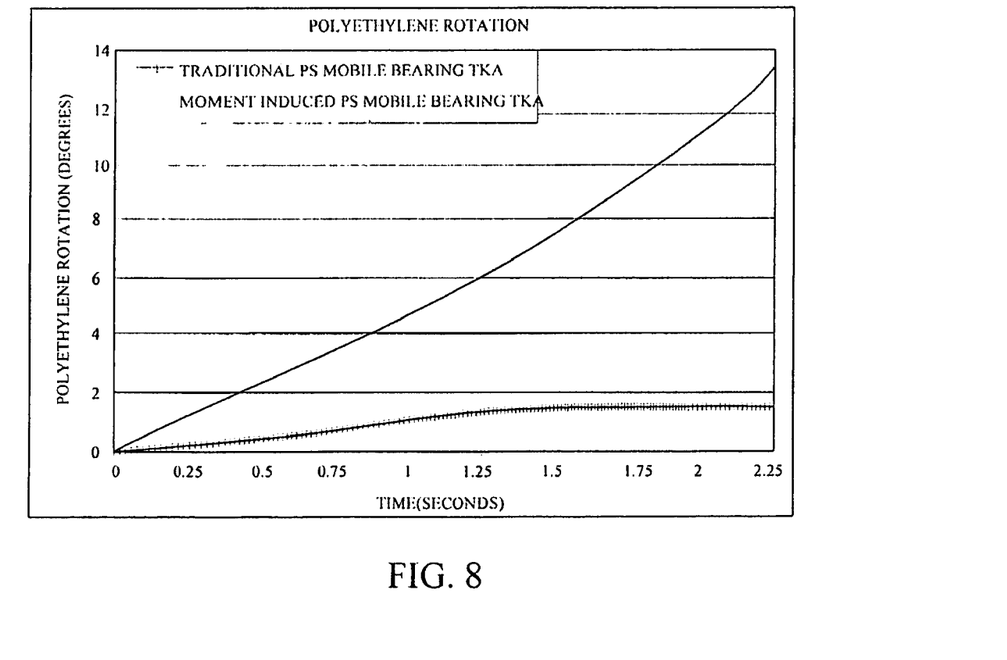
FIG. 8 is a plot of polyethylene rotation versus time for a prior art polyethylene tibial insert having the post and the rotation point in the center of the polyethylene, and the new moment induced posterior stabilized mobile bearing total knee arthroplasty prosthetic insert showing substantially greater rotation.

The amount of offset created between the post 602 and the rotation point O of the MITKA prosthetic insert 600 leads to increased axial rotation of the tibial insert relative to the tibial implant component (not shown) in the clockwise direction (T3> direction). An exemplary mathematical model has determined that a 3 mm shift of the post 602 in the medial direction from the centerline in the medial-lateral direction and a 3 mm shift of the rotation point O in the lateral direction from the centerline in the medial-lateral direction leads to 5 to 13 degrees of normal axial rotation, depending on the weight of the patient, the balancing of the knee, and the amount of force applied by the cam on the post (see FIG. 8). A second analysis was conducted using the exemplary mathematical model where the post 602 was shifted 6 mm in the medial direction and the rotation point O was shifted 6 mm in the lateral direction. The results for this analysis revealed the amount of normal axial rotation of the polyethylene increased to a range of 10 to 22 degrees of normal axial rotation, again, depending on the weight of the patient, the balancing of the knee, and the amount of force applied by the cam on the post. A third analysis, where the post 602 was shifted 10 mm in the medial direction and the rotation point O was shifted 10 mm in the lateral direction lead to normal axial rotation of the polyethylene ranging between 20 to 35 degrees, in the clockwise direction. Greater shifts in the medial and lateral direction are also within the scope of the disclosure, such as, without limitation, 0.01 to 20 millimeters of medial or lateral shift.

Figure 9:
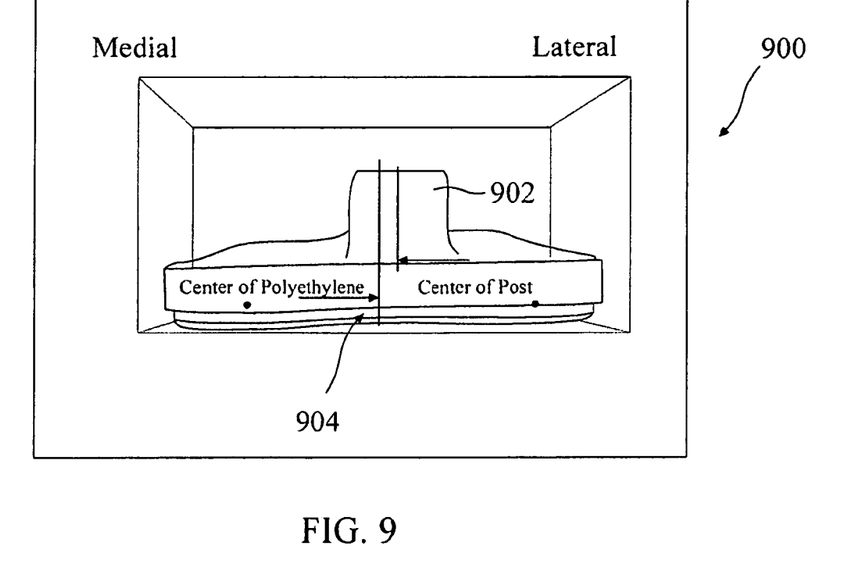
FIG. 9 is a rear profile view of a first exemplary moment induced fixed bearing posterior stabilized total knee arthroplasty prosthetic insert in accordance with the present invention.

Referencing FIG. 9, an exemplary posterior stabilized fixed bearing Moment Induced Total Knee Arthroplasty (MITKA) prosthetic insert 900 in accordance with an exemplary embodiment includes a cam/post mechanism 902 shifted in the lateral direction from the medial-later center 904 of the tibial insert. It is to be understood that the corresponding cam of the femoral component would be likewise shifted in the lateral direction to accommodate the shifted tibial post.

Figure 10:
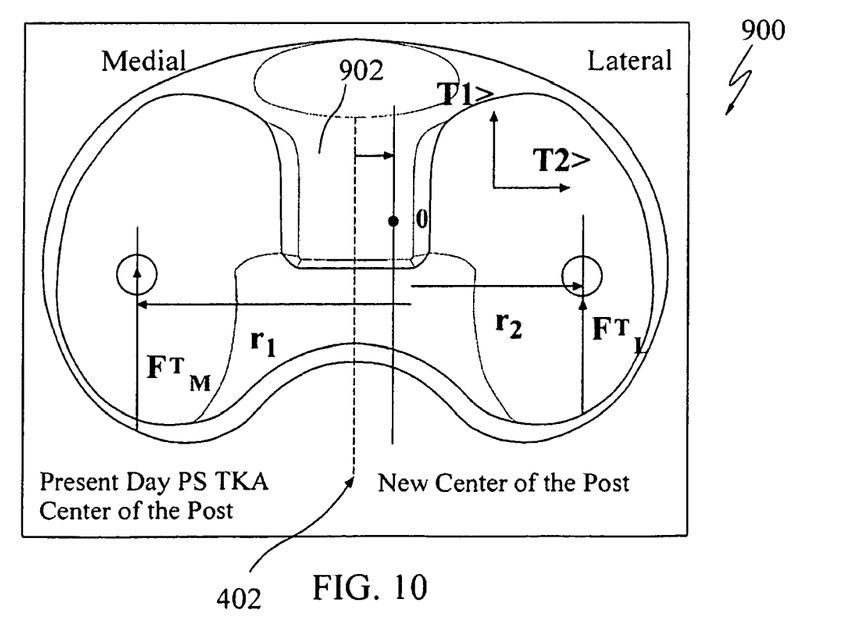
FIG. 10 is an overhead view of a first exemplary moment induced fixed bearing posterior stabilized total knee arthroplasty prosthetic insert in accordance with the present invention.

Referring to FIG. 10, a moment analysis of the exemplary fixed bearing PS MITKA prosthetic 900 insert includes summating the moments, around point of rotation O, in the T3> direction. The moment equation is represented by Equation #19:

$$\Sigma M_o \cdot T3 >= -r1 \cdot T2 > \times F^T_M \cdot T1 > + r_2 \cdot T2 > \times F^T_L \cdot T1 > \quad \text{Equation \#19:}$$

Where the following information is known, the distance $r1 = 2r$, $r2 = r$, and the forces $F^T_M = F^T_L = F$, Equation #19 can be further simplified into Equation #20:

$$\Sigma M_o \cdot T3 >= -2rF \cdot (-T3>) + rF \cdot (-T3>),$$

$$\Sigma M_o \cdot T3 >= 2rF \cdot T3 > - rF \cdot T3 >$$

$$\Sigma M_o \cdot T3 >= rF \cdot T3 > \quad \text{Equation \#20:}$$

In this exemplary moment summation, the moment induced by the exemplary MITKA prosthetic insert 900 is equal to rF, in the clockwise direction (looking down), leading to normal axial rotation of the femur relative to the tibial insert.

The amount of offset created between the post 902 and the rotation point O of the MITKA prosthetic insert 900 leads to increased axial rotation of the tibial insert relative to the tibial implant component (not shown) in the clockwise direction (T3> direction). An exemplary mathematical model has determined that a 3 mm shift of the post 902 in the lateral direction from the centerline in the medial-lateral direction leads to a femoral component rotation in the range of 2 to 8 degrees, depending on the weight of the patient, the balancing of the knee, and the amount of force applied by the cam on the post. If the post 902 is shifted 6 mm in the lateral direction, the amount of femoral component rotation increased to a range of 5 to 13 degrees, and if the post 902 was shifted 10 mm in the lateral direction, the amount of axial rotation again increased to a range of 9 to 25 degrees. Greater shifts in the medial and lateral direction are also within the scope of the disclosure, such as, without limitation, 0.01 to 20 millimeters of medial or lateral shift.

As discussed previously, the cam/post mechanism can be used in a posterior stabilized TKA prosthetic to generate rotation by creating a moment arm from the rotation point to the post of a mobile bearing TKA, or by shifting the post laterally, increasing the moment arm from the post to the medial condyle shear force. In the posterior cruciate retaining TKA, moments are primarily induced by offsetting the rotation point and building up conformity between the femoral radii and the concave tibial insert radii.

Figure 11:
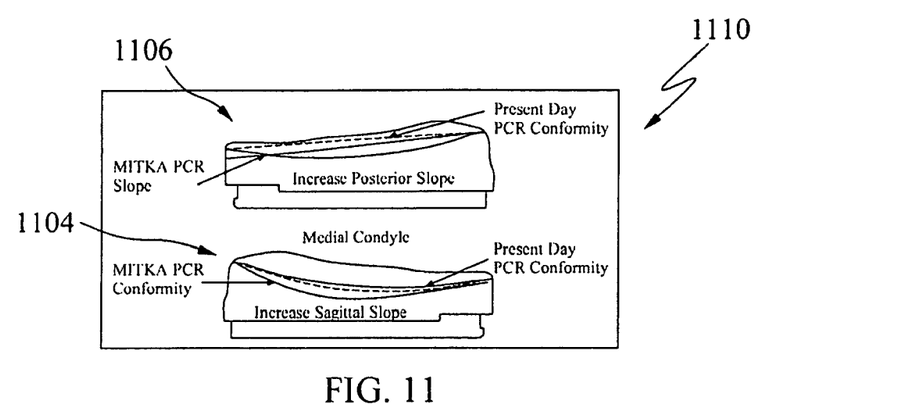
FIG. 11 are medial and lateral profile views of exemplary changes in medial condyle conformity and increased lateral condyle posterior slope for the exemplary prosthetic inserts of the present invention.

Referencing FIG. 11, an exemplary MITKA posterior cruciate retaining (PCR) fixed bearing prosthetic insert 1100 in accordance with the present disclosure includes a medial receiver 1104 and a lateral receiver 1106 that are adapted to receive the medial and lateral condyles, respectively, of a femoral prosthesis (not shown). In order to rotate the tibial insert 1100 clockwise (looking down), the insert 1100 includes greater conformity between the medial condyle and the medial receiver 1104 on the medial side of the tibial insert. In this exemplary embodiment 1100, the radii of the medial receiver 1104 is greater than the radii of the medial condyle, allowing for anterior/posterior translation to occur between the medial condyle and the medial receiver. Increased conformity between the medial receiver 1104 and the medial condyle leads to an increased shear force applied by the medial condyle on the medial receiver of the polyethylene insert, causing a clockwise moment to occur, especially if the superior surface of lateral side of the tibial insert 1100 is either flat or convex in shape, coupled with a flatter shape for the lateral condyle of the femoral prosthesis.

Figures 12A, 12B, 12C:
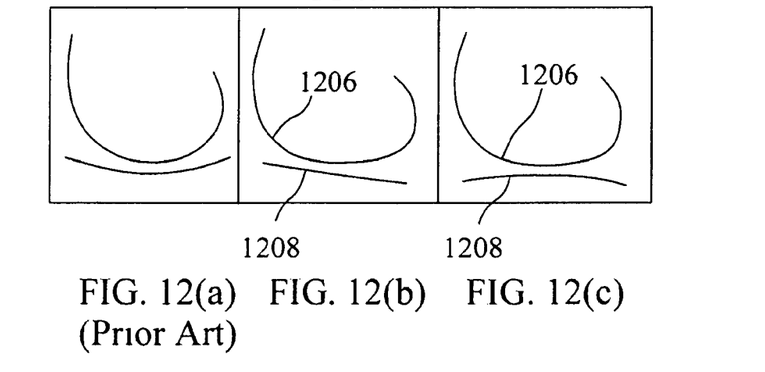
FIG. 12(a) is a pictorial representation of a prior art lateral femoral condyle PCR TKA prosthetic having a rounded convex shape.
FIG. 12(b) and FIG. 12(c) are pictorial representations of an exemplary MITKA PCR prosthetic having femoral radii for the lateral condyle being flatter, in contact with either a convex or sloped downward in the posterior direction tibial component.
Figure 13:
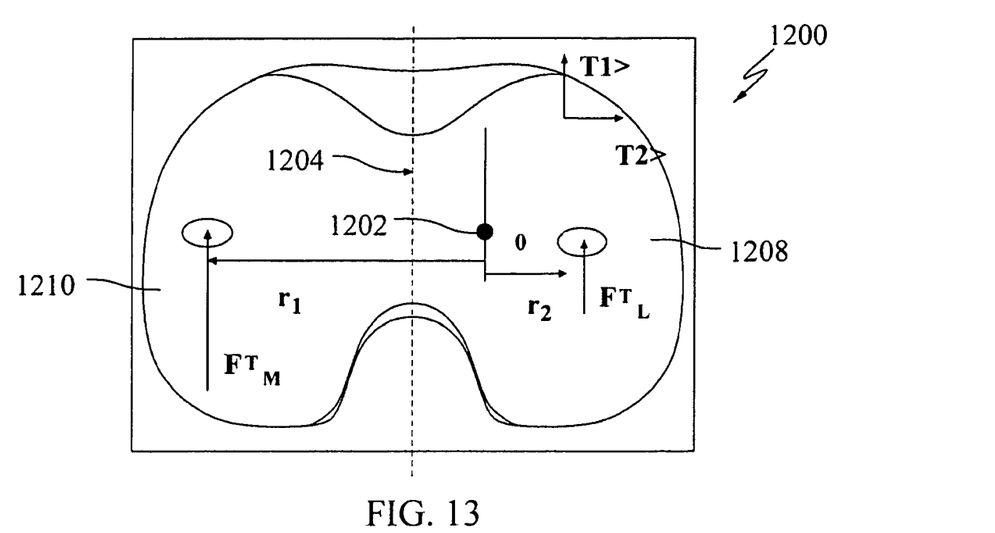
FIG. 13 is an overhead view of a first exemplary moment induced mobile bearing posterior stabilized total knee arthroplasty prosthetic insert in accordance with the present invention.

Referencing FIGS. 12 and 13, an exemplary MITKA mobile bearing PCR prosthetic insert 1200 includes the rotation point 1202 (and rotational axis) moved in the lateral direction with respect to the center 1204 of the tibial implant baseplate (not shown) using the contours between the insert 1200 and the femoral condyles 1206, 1208. On the lateral side, the lateral femoral condyle 1206 is flatter (similar to the shape of a canoe) and the lateral receiver 1208 of the tibial insert is either sloped downward in the anterior-to-posterior direction (see FIG. 12(*b*)) or convex (see FIG. 12(*c*)). On the medial side, the medial femoral condyle includes greater conformity with the medial receiver 1210 on the medial side of the tibial insert 1200. Therefore, as the shear force between the femoral condyles and the tibial insert increases, the amount of shear force will be greater on the medial side and induce a clockwise rotation of the tibial insert due to: (1) the increased conformity; and (2) the moment arm from the rotation point to the medial shear force being greater than the moment arm from the rotation point to the lateral condyle force.

One of the main goals for achieving increased weight-bearing flexion for a total knee arthroplasty is the ability to move the lateral condyle in the posterior direction. In the normal knee, this can be achieved through axial rotation or translation of both condyles. Since, in the normal knee, the medial condyle does not move more than 10 mm in the posterior direction and on average, this amount is less than 5 mm, the lateral condyle achieves posterior contact through femorotibial axial rotation. Moments are introduced in the MITKA so that normal axial rotation could occur and the lateral condyle can achieve greater posterior contact with increasing knee flexion. This inducement of moments is more easily accomplished with a posterior stabilized TKA, where the cam/post force could be used to drive rotation in the clockwise direction or to lever the medial condyle force with respect to the post. In the posterior cruciate ligament retaining TKA, the ability to induce moments is more involved. The MITKA posterior cruciate ligament retaining knee uses increased conformity between the medial condyle and the medial receiver of the polyethylene insert. Also, an increased radius of curvature for the lateral condyle (canoe shaped) allows the lateral condyle contact point to move in the posterior direction within the first 30 degrees of knee flexion. Therefore, the goal of achieve posterior contact with the lateral condyle, with increasing knee flexion can be accomplished in MITKA posterior cruciate ligament retaining TKA through the introduction of moments and by changing the geometrical shapes of the femoral condyles. In this manner, the axis of rotation between the MITKA mobile bearing PCR prosthetic insert 1200 and the femoral prosthetic can be shifted from the medial-lateral centerline of the insert 1200 (and also from the anterior-posterior centerline), while the axis of rotation between the MITKA mobile bearing PCR prosthetic insert 1200 and the tibial prosthetic tray (not shown) can be shifted from the medial-lateral centerline of the insert 1200 (and also from the anterior-posterior centerline of the insert 1200).

Although the increased conformity between the medial condyle and the receiver in medial aspect of the tibial polyethylene insert and the flatter lateral condyle, contacting either a posterior sloped or convex shaped lateral aspect of the polyethylene insert has been previously described herein for a posterior cruciate retaining TKA, these design features can be used in any TKA prosthetic type. The above mentioned design changes could be used in a PS TKA type to increase axial rotation and could be used in an anterior and posterior cruciate retaining TKA type to ensure normal axial rotation.

In the exemplary prosthetic inserts of the present disclosure, the amount of medial condyle conformity with respect to the medial receiver of the tibial insert may play a significant role. An additional factor that may play a significant role in axial rotation, leading to an increase or decrease in the amount of axial rotation described herein, is condylar balancing at the time of surgery. It is to be understood that the mathematical models referenced in the aforementioned discussion incorporated medial and lateral condyle flexion gaps, during intra-operative ligament balancing, that were equal, leading to the medial condyle contact force being equal to the lateral condyle contact force. If the medial condyle contact force is greater than the lateral condyle contact force, the amount of normal axial rotation would increase over those values predicted by the above-referenced mathematical model. In contrast, if the lateral condyle contact force is greater than the medial condyle contact force, the amount of axial rotation would fall below those values predicted by the model.

Figure 14:
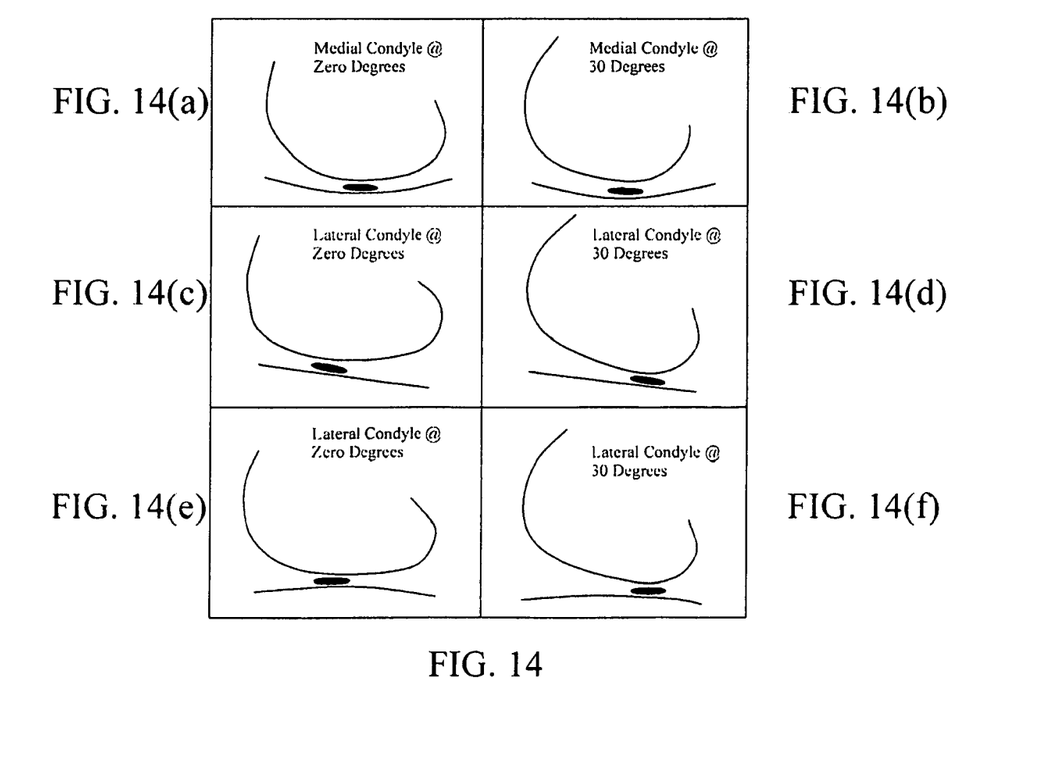

Referencing FIG. 14, the exemplary MITKA posterior cruciate retaining TKA prosthetic includes increased conformity between the medial condyle and the medial receiver of the tibial (polyethylene) insert in order to induce a clockwise moment of the femur relative to the tibia (normal axial rotation) (see FIGS. 14(*a*) & (*b*)). Also, the lateral condyle will achieve greater posterior motion due to the flatter condylar geometry (canoe shaped) at full extension leading a rapid change of the contact position from full extension to 30 degrees of knee flexion. This posterior change of the contact position for the lateral condyle may be further assisted by the increased posterior slope of the polyethylene insert (see FIGS. 14(*c*) & (*d*)) or the convex shape of the polyethylene insert (see FIGS. 14(*e*) & (*f*)).

Figure 15:
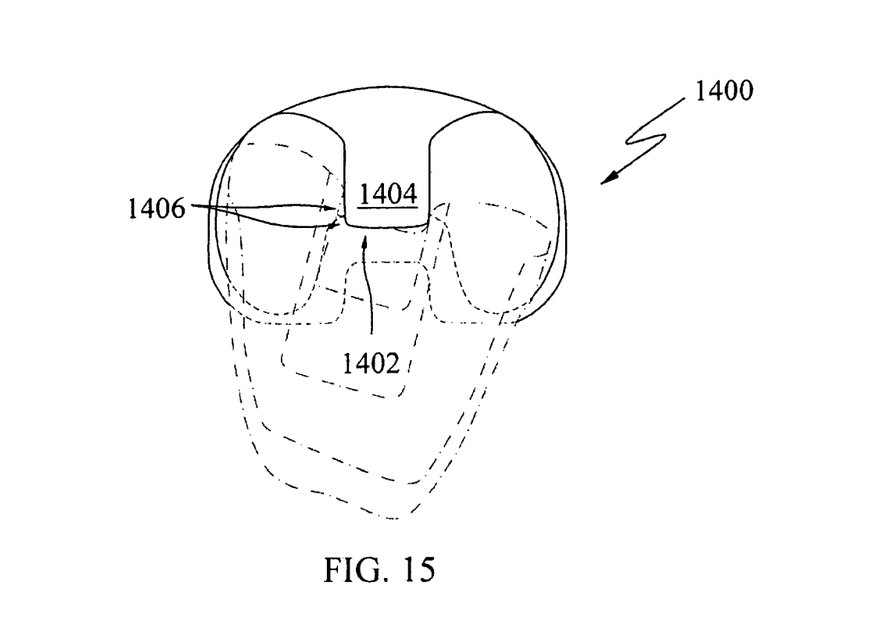
FIG. 15 is a 3-D overhead, perspective view of a prior art TKA prosthetic cam/post mechanism with flat leading surfaces.

Referring to FIG. 15, all cam/post mechanisms in present-day TKA prosthetics 1400 include flat surfaces. These flat surfaces lead to the hypothesis that the contact areas would be large, thereby leading to less stress applied by the cam 1402 onto the post 1404. Unfortunately, if rotation of the femoral component (the cam) 1402 occurs with respect to the tibial insert (the post) 1404 in a fixed bearing posterior stabilized TKA prosthetic, the opposite is true and the contact area 1406 between the femoral cam and the tibial post becomes very small. A primary concern for decreased contact areas between the flat cam 1402 on a flat post 1404 is edge loading, leading to high stresses that lead to premature tibial insert failure at the post.

Figure 16:
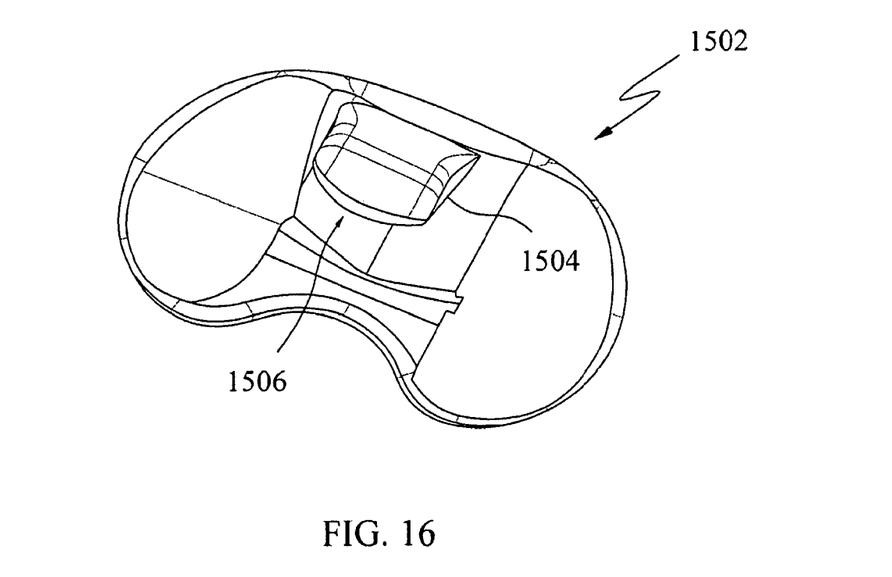
FIG. 16 is an elevated perspective view of an exemplary MITKA posterior stabilized prosthetic insert.
Figure 17:
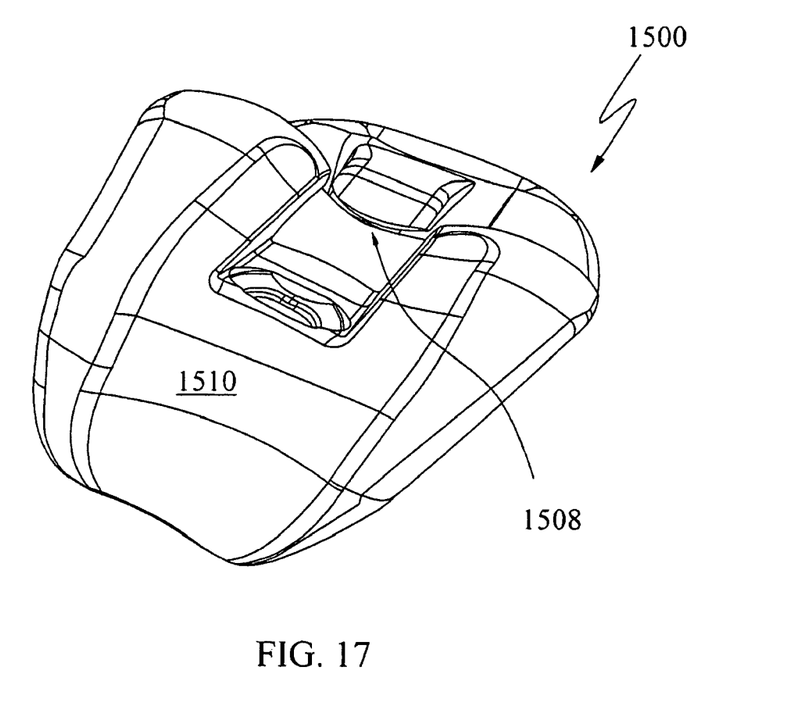
FIG. 17 is an elevated perspective view of an exemplary MITKA posterior stabilized prosthetic device.

Referencing FIGS. 16 and 17, an exemplary MITKA posterior stabilized TKA prosthetic device 1500 in accordance with the present disclosure includes a tibial insert 1502 with a tibial post 1504 having a rounded posterior surface 1506. This rounded posterior surface 1506 of the post 1502 is adapted to interact with a rounded femoral cam 1508 of a femoral prosthetic component 1510. The radius R for the rounded posterior surface 1506 of the post 1504 and the rounded cam 1508 are the similar, but the chosen value of R for the MITKA fixed bearing posterior stabilized prosthetic device 1500 will depend on the amount of rotation desired. If the MITKA posterior stabilized prosthetic device 1500 is designed to incorporate minimal femorotibial axial rotation, then the value for R will be higher than the value for R if the MITKA posterior stabilized prosthetic device 1500 is designed for greater axial rotation.

While the aforementioned exemplary MITKA posterior stabilized prosthetics have been explained using a tibial component with an integral post that is adapted to interface with a cam of the femoral prosthetic component, it is also within the scope of the disclosure to incorporate the post into the femoral component and the cam into the tibial insert. Likewise, while the aforementioned exemplary prosthetics have been explained using a tibial component with an integral post adapted to interface with a cavity within the tibial insert, it is also within the scope of the disclosure to incorporate the post into the tibial insert, where the post would be correspondingly received by a cavity within the tibial implant.

While the aforementioned exemplary MITKA mobile bearing POR prosthetics have been explained by shifting the post and point of rotation between the insert and tibial component, it should be understood that one might only shift the post or only shift the point of rotation to create the moments discussed herein. An exemplary embodiment would include a POR prosthetic device having a post aligned along the medial-lateral midline, while the point of rotation between the insert and tibial component (tray) would be offset from the medial-lateral midline. Conversely, an exemplary POR prosthetic device may have its point of rotation aligned along the medial-lateral midline, while the post would be offset from the medial-lateral midline.

It is also within the scope of the disclosure to shift of the contact point of the post or point of rotation anteriorly or posteriorly. Mobile bearing prior art prosthetic knee inserts have always had the point of rotation centered along the medial-lateral midline and along the anterior-posterior midline. By shifting the contact point of the post or point of rotation from the prior art centered position, moments are introduced if the point of contact of the post and point of rotation are not coaxial.

Those skilled in the art will readily understand that the exemplary inserts of the instant disclosure are adapted for use in prosthetic knee joints comprising tibial and femoral components. The plethora of tibial implants and femoral implants that the exemplary embodiments of the instant disclosure may be incorporated with, or used in place of, defies an exhaustive listing.

Following from the above description and exemplary embodiments, it should be apparent to those of ordinary skill in the art that, while the methods and apparatuses herein described constitute exemplary embodiments, the invention is not limited to these precise embodiments and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A fixed bearing prosthetic knee joint system comprising:
a distal femoral implant component having a medial condyle, a lateral condyle, and a cam positioned between the medial and lateral condyles; and
a tibial component comprising a tibial tray and a fixed bearing tibial insert mountable on the tray to be fixed against rotation, the fixed bearing tibial insert having a medial condyle receiver, a lateral condyle receiver, and a stabilizing post positioned to engage the cam of the femoral implant component during articulation;
wherein:
the lateral condyle receiver is flatter than the medial condyle receiver;
the medial condyle has a medial condyle radius and the medial condyle receiver has a medial receiver radius that is greater than the medial condyle radius of the medial condyle to permit anterior/posterior translation to occur between the medial condyle and the medial condyle receiver;
the fixed bearing tibial insert has a medial-lateral centerline;
the stabilizing post has an anterior surface having a center;
the center of the anterior surface of the stabilizing post is offset laterally from the medial-lateral centerline of the fixed bearing tibial insert.

2. The fixed bearing prosthetic knee joint system of claim 1 wherein:
the lateral condyle receiver includes at least one of a convex shape or a sequentially sloped from anterior to posterior shape; and
the medial condyle receiver includes a concave shape.

3. The fixed bearing prosthetic knee joint system of claim 1 wherein the medial condyle is larger than the lateral condyle.

4. The fixed bearing prosthetic knee joint system of claim 1 wherein the center of the anterior surface of the stabilizing post is laterally offset between about 0.1 millimeters to about 20 millimeters from the medial-lateral centerline of the fixed bearing tibial insert.

5. The fixed bearing prosthetic knee joint system of claim 1 wherein the stabilizing post has a posterior aspect that is rounded to have a concave or convex shape.

6. The fixed bearing prosthetic knee joint system of claim 1 wherein the lateral condyle is flatter than the medial condyle.

* * * * *